United States Patent [19]
Martinelli

[11] Patent Number: 4,977,655
[45] Date of Patent: Dec. 18, 1990

[54] METHOD OF MAKING A TRANSDUCER

[75] Inventor: Michael A. Martinelli, Winchester, Mass.

[73] Assignee: Intra-Sonix, Inc., Burlington, Mass.

[21] Appl. No.: 340,383

[22] Filed: Apr. 18, 1989

Related U.S. Application Data

[60] Division of Ser. No. 151,394, Feb. 2, 1988, which is a continuation-in-part of Ser. No. 129,830, Dec. 8, 1987, Pat. No. 4,821,731, which is a continuation-in-part of Ser. No. 856,621, Apr. 25, 1986, abandoned.

[51] Int. Cl.⁵ ............................................... A61B 8/12
[52] U.S. Cl. ................. 29/25.35; 128/662.06
[58] Field of Search ................... 29/25.35; 128/662.06

[56] References Cited

U.S. PATENT DOCUMENTS

| | | | |
|---|---|---|---|
| 3,128,532 | 4/1964 | Massa | 29/25.35 |
| 3,821,834 | 7/1974 | McElroy | 29/25.35 |
| 4,704,774 | 10/1987 | Fujii et al. | 29/25.35 |

Primary Examiner—Francis Jaworski
Attorney, Agent, or Firm—Schiller, Pandiscio & Kusmer

[57] ABSTRACT

A miniature transducer designed for use in a medical imaging system catheter probe is disclosed. The transducer has an electric cavity and coaxial construction for preventing electric fields from being emitted or received by the transducers. The construction of the transducer enables two to be mounted very close to one another on a thin catheter probe, one for transmitting acoustic pulses and the other for sensing echoes in response to the acoustic pulses, for imaging extremely close targets. The transducers can be secured to the catheter probe in such a way as to substantially acoustically isolate one from the other.

A method of making the transducer by applying several electrically-conductive and insulating coatings and layers to a core in selected sequence so as to create a transducer having an electrical cavity, coaxial construction.

22 Claims, 4 Drawing Sheets

METHOD OF MAKING A TRANSDUCER

RELATED APPLICATIONS

This application is a divisional application of U.S. application, Ser. No. 151,394, filed Feb. 2, 1989 and now U.S. Pat. No. 4,862,893, which in turn is continuation-in-part of co-pending application U.S. application Ser. No. 129,830 filed Dec. 8, 1987 in the names of Michael Martinelli and Peter von Thuna (hereinafter referred to as the "Parent Application"), the latter application being a continuation-in-part of U.S. application Ser. No. 856,621 filed Apr. 25, 1986 in the names of Michael Martinelli, Thomas Aretz, John Butterly and Stanley M. Shapshey.

FIELD OF THE INVENTION

The present invention relates generally to electro-acoustical devices for converting electrical energy into acoustical energy and vice versa, and more particularly to a miniature transducer, an improved system utilizing such transducers for imaging internal features of various parts of a body and, a method of making such transducers.

BACKGROUND OF THE INVENTION

Devices are known which use pulse-echo ultrasound to provide information regarding the thickness, configuration, composition and other characteristics of internal features of various parts of a body. Such a device is described, for instance, in U.S. Pat. No. 4,576,177 to Webster. However, specific problems are encountered when utilizing pulse-echo ultrasound to acquire information with sufficiently high resolution in extremely close range applications, such as acquiring information relating to the walls of coronary arteries.

More specifically, in known long range ranging systems, such as pulse-echo radar or sonar, a single electro-acoustical device is typically used for transmitting the sounding pulses and receiving the echoes. The device is switched between transmit and receive modes using a TR switch. The latter is designed to operate so as to minimize any interference during the receive mode caused by the excitation of the electro-acoustic device during the transmit mode. For example, the instant the device stops transmitting it may continue to ring. Accordingly, in order to receive any echo signals it is important that the device be allowed to stop ringing before the device is switched to the receiving mode. The TR switch can be operated quickly to quench the device at the termination of the transmit mode in order to switch the device to the receive mode. However, a finite time is nevertheless required to expire before the electro-acoustic device is sufficiently quiescent in order to operate in the receive mode without residual interference from the transmit mode. This finite time, called "dead space", thus creates a minimum time the receiver must be turned off following the end of the transmit mode. In other words, the target distance must be sufficiently large so that echoes are not received by the electro-acoustic device until after the time of the dead space has elapsed. The dead space therefore creates a minimum target distance at which the ranging device will operate without cross interference between the two modes and without a loss of information. This is usually not a problem for typical radar and sonar applications where target distances are well beyond the minimum distance required.

In an effort to improve short range performance, some short range pulse-echo ranging systems have resorted to using separate transmitter and receiver devices. The amount of excitation from the transmit pulse resident in the receive channel is naturally reduced by the physical isolation of the two (often by physically spacing one a relatively large distance from the other) and, hence, the switching need not be so complete as is the case when a single device is used to transmit and receive. Additional improvements can be achieved by utilizing improved materials which exhibit reduced ringing. For example, as described hereinafter, certain plastic materials have been found particularly useful in medical imaging applications because of the reduced acoustic impedance of such materials relative to known crystalline materials. However, such systems are still range limited by the required dead space, and the physical separation of the two transmitter and receiver devices. Therefore, until the present invention the use of separate transmitter and receiver devices for pulse-echo ultrasonic acquisition of information regarding very close range targets, such as the walls of coronary arteries, has been impractical.

More specifically, the system disclosed in the Parent Application comprises a catheter probe that is adapted to be inserted into a part of a body, and is particularly good at providing relatively high resolution imaging data of an relatively small, predetermined portion of the body, such as a small section of a coronary artery (the catheter may also be adapted to deliver laser energy to the interior of the body part for modifying internal features thereof, e.g., removing plaque deposits from a coronary artery). A transducer assembly is attached to the distal end of the catheter for emitting and receiving acoustic pulses used in generating imaging information. Sets of imaging data are created by moving the catheter axially along and rotationally about its axis, within the body section of interest, through a series of imaging locations, while the transducer assembly is actuated to emit a train of acoustic pulses and responsively receive a series of acoustic echoes at each imaging location. By also continuously sensing the location of the catheter, and relating the set of data to the respective location where it was generated, an image of the internal features of the body part may be generated.

It is clear that the target being imaged by the system disclosed in the Parent Application is extremely close to the transducer assembly. In fact the transducer assembly is frequently almost in contact with the targeted surfaces, such as the inner surface of the wall of an artery. At such close range, relying on standard radar and sonar techniques of allowing the required time of dead space to transpire after the transmit mode and before switching to a receiving mode is inadequate since the target ranges are well below the minimum range for the dead space required and imaging data will be lost during this time. Utilizing two transducer devices, one for transmitting and one for receiving, does not alone overcome the problem since the two devices must be mounted on the end of a catheter extremely close to one another. Because of the close proximity between the two devices, sufficient dead space still must be provided to prevent acoustic interference, such as acoustic cross talk, between the transmitting device and receiving device, as for example when the transmitting device is ringing following the generation of an acoustic pulse. In fact, because of the close proximity of the two, certain electrical interference problems can occur between the transmitting and receiving devices which do not occur with a single device, such as capacitive and inductive coupling between the two devices.

OBJECTS AND SUMMARY OF THE INVENTION

It is a principal object of the present invention to provide an improved electro-acoustic device adapted to overcome or substantially reduce the above-noted problems.

It is another object of the present invention to provide an improved electro-acoustic device capable of operating as a transmitting or receiving device in a close range ranging system such as described in the Parent Application.

Still another object of the present is to provide an improved electro-acoustic device constructed and mounted to be substantially acoustically and electrically isolated, so that two such devices can be used respectively as transmitting and receiving devices in relatively close proximity to one another for use in a relatively close range ranging system, such as the system described in the Parent Application.

Yet another object of the present invention is to provide an improved electro-acoustic device constructed and mounted so as to substantially reduce the amount of ringing of the device following the transmission of an acoustic pulse, and substantially prevent the generation of stray electric fields.

And still another object of the present invention is to provide a method of making such a transducer.

And yet another object of the present invention is to provide a catheter probe including a transmitter electro-acoustic transducer and a receiver electro-acoustic transducer so that extremely close objects can be imaged in accordance with the system described in the Parent Application;

And still another object of the present invention is to provide such a catheter of the type described in the Parent Application in which the acoustic pulses are transmitted and received by a pair of transducer devices which are substantially acoustically and electrically isolated from one another.

These and other objects are achieved by a novel miniature electro-acoustic transducer, a novel method of making the transducer, and an improved catheter probe having a pair of such transducers for generating acoustic information used to image internal features of a body part.

The transducer has a novel coaxial and closed electrical cavity construction for electrically shielding the transducer.

The transducer is designed for use in pairs on an imaging system catheter of the type described in the Parent Application. A pair of the transducers of the present invention are mounted on the distal end of the catheter in such a manner so as to minimize acoustic interference between the transducers.

Other objects of the invention will in part be obvious and will in part appear hereinafter. The invention accordingly comprises the processes involving the several steps and the relation and order of one or more of such steps with respect to each of the others, the product possessing the features, properties and relation of components, and the apparatus possessing the construction, combination of elements and arrangement of parts, all of which are exemplified in the following detailed disclosure, and the scope of the application of which will be indicated in the claims.

For a fuller understanding of the nature and objects of the present invention, reference should be had to the following detailed description taken in connection with the accompanying drawings, wherein:

BRIEF DESCRIPTION OF THE DRAWINGS

The configuration and relative dimensions of the various layers and elements illustrated in the drawings have been modified for clarity of illustration and description. In the drawings the same reference numerals are used to refer to the same and like parts.

DETAILED DESCRIPTION OF THE INVENTION

Figure 1:
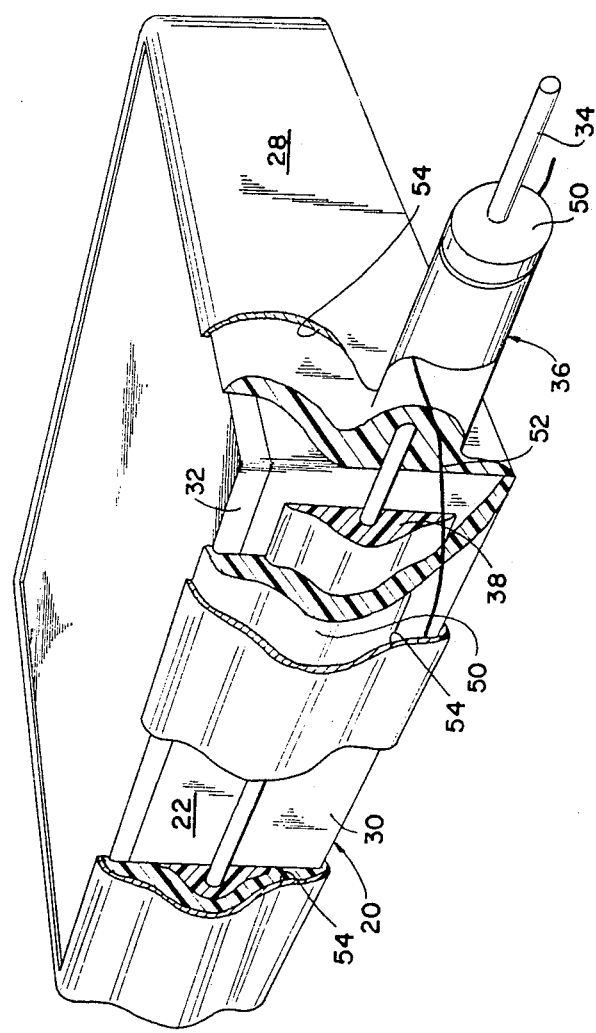
FIG. 1 is a perspective view of the preferred embodiment of the transducer of the present invention, partially broken away to expose internal features thereof.

The preferred embodiment of the transducer of the present invention is illustrated in FIG. 1. The transducer comprises an inner core or substrate 20 and a piezoelectric device 32 disposed on the substrate. The transducer is constructed so that it is electrically shielded such that two such transducers are capable of operating adjacent one another, with on transducer operating as a transmitting device and the other as a receiver device without significant electrical interference. Further, as will be more evident hereinafter, the two transducers can be suitably mounted on a catheter 100 (as described in greater detail hereinafter with respect to FIGS. 9 and 10) so that the two transducers are substantially acoustically isolated from one another.

More specifically, substrate 20 is preferably made from a suitable ceramic material, such as alumina, i.e., aluminum oxide. The substrate is shown in the drawings as a rectangular block or brick comprising a front surface 22 (FIGS. 1 and 2), a top surface 24 (FIG. 2), a left side surface 26 (FIG. 3), a right side surface 28 (FIG. 3), a bottom surface (not shown) opposite top surface 24, and a rear surface (not shown) opposite front surface 22. It should be appreciated, however, that the exact configuration of the substrate can vary depending upon the application for which the transducer is intended to be used.

Since the transducer is preferably designed for use on a catheter of an imaging system of the type described in the Parent Application, the size of the transducer must be relatively small. Where the imaging system is designed to image selected portions of coronary arteries, the substrate 20 is dimensioned so that it is thick enough to function as an acoustic reflector for the piezoelectric device 32. In the preferred embodiment where the piezoelectric device is a polymer piezoelectric device (as described hereinafter), the substrate is dimensioned on the order of about 0.028 inches wide, 0.038 inches long, and 0.012 inches thick, although I believe, at least in the case of alumina, the substrate can be made even thinner. The minimum thickness of the substrate is limited by the acoustic reflectivity of the substrate material for the piezoelectric device 32 and the acoustic impedance mismatch between the two. For alumina at the acoustic frequency of interest (in the megahertz region), the minimum thickness is believed to be about 0.006 inches thick at which dimension the substrate still adequately functions as a reflector for acoustic energy generated by the piezoelectric device 32 disposed on the substrate. Decreasing the thickness to less than 0.006 inches reduces the ability of the substrate to reflect the acoustic energy to the point where a substrate of 0.003 inch thickness will cease to function as an adequate reflector so that substantially all of the acoustic energy transmitted by the device 32 downwardly will be transmitted through the substrate. As discussed hereinafter, the relatively small size of the transducer is made possible because of the material from which the piezoelectric device 32 is made, and more particularly, its relatively close impedance match to that of body fluids.

In the preferred embodiment of the invention the front surface 22 and top surface 24 are coated with an electrically conductive coating 30, preferably in the form of a metallized cladding, such as vapor deposited gold or a heat sintered metal cladding (such as granulated nickel), so as to provide an electrical connection between the front surface and the top surface. Preferably, coating 30 is about 0.2 mil inches thick although the thickness can vary depending upon the material and application of the transducer.

In one embodiment of the present invention a sheet or coating 33 of dielectric material having piezoelectric characteristics, and forming the center dielectric material of the piezoelectric device 32, is secured to coating 30 on top surface 24. In sheet form the dielectric material may be secured, for example, with an electrically conductive epoxy, so that coating 30 forms the bottom electrode of the piezoelectric device. Alternatively, where the piezoelectric material is of a type that can be applied as a coating, e.g., such as the materials described below, the sheet can be deposited as a coating of substantial uniform thickness over the coating 30. As will be more evident hereinafter, the top electrode of the piezoelectric device 32 is provided when the outer coating 54 of electrically conductive material is provided over the top surface of the sheet 33.

Sheet 33 is made of a material which preferably has an acoustic impedance that closely matches the acoustic impedance of body fluids and water, but provides a substantial impedance mismatch with the material of the substrate. Certain plastic or polymer piezoelectric materials, such as polyvinylidene fluoride (PVDF) or similar copolymer materials such as PVF2 are satisfactory. The latter materials have an acoustic impedance (defined as the complex ratio of the sound pressure on a given surface to the sound flux through that surface) of about 4.3 million Rayleighs ($4.3 \times 10^6$ kg/(m$^2$s)), while the acoustic impedance of blood and other body tissues is in the order of 1.5 million Rayleighs. As described hereinafter in greater detail with respect to FIG. 9, the final match between these two is accomplished by a one-quarter wave anti-reflective intervening layer of plastic film disposed over the top of the transducer. This is substantially close when one considers that the acoustic impedance of a PZT crystal material has an acoustic impedance in the order of 30.0 million Rayleighs. The reflectivity of the substrate is also a function of the acoustic impedance mismatch between the substrate and the piezoelectric device. Alumina has an acoustic impedance of about 40 million Rayleighs which provides a greater mismatch, and therefore is more reflective, with the polymeric materials described, then would be provided by a PZT crystal material. For a description of the advantages of polymer piezoelectric materials over ferro-electric ceramic materials in transducers for medical ultrasound applications, see generally Lancee, C.T.; Souquet, J.; Ohigashi,-H.; and Bom, N.; "Ferro-electric Ceramics Versus Polymer Piezoelectric Materials" presented as a paper during the fifth Symposium on Echocardiology held in Rotter Dam, The Netherlands, in 1983. It should be appreciated that the piezoelectric device 32 can be preformed by providing a sheet 33 with electrodes previously formed respectively on its top and bottom surfaces before it is secured to the coating 30. For example, a 52 micron thick polyvinylidene fluoride (PVDF) foil of the type manufactured and sold by Pennwalt Corporation of King of Prussia, PA, under the tradename KYNAR Piezo Film, would be satisfactory.

The inner conductor or core wire 34 of coaxial line 36 is preferably attached to front surface 22 using an electrically-conductive glue 38, e.g. a silver-filled room-temperature Vulcanizable (RTV) glue, so as to be electrically connected to metallized coating 30 on front surface 22. The wire 34 is preferably mounted to extend substantially parallel with the top and bottom surfaces of the transducer and normally to the left and right side surfaces of the transducer. In the embodiment of the transducer used in the imaging system of the Parent Application, core wire 34 is about 0.001 inch in diameter, and because of its thinness is preferably made of a high strength electrically conductive material such as the nickel-copper alloy of the type manufactured under the trademark Monel by the International Nickel Co. Inc. of Huntington, WV or the nickel-chromium-aluminum-copper alloy of the type manufactured under the trademark Evanohm by Wilbur B. Driver Company, Newark, NJ., or other suitable, high strength electrically-conductive material. The electrically conductive glue 38 is applied only on front surface 22, and care is taken so that the glue does not extend into contact with piezoelectric sheet 33 (or the upper electrode where the device is preformed before being mounted on the top of the substrate).

An electrically insulating conformal coating 50 covers core wire 34, glue 38, front surface 22, left side surface 26, right side surface 28 and the back and bottom surfaces of core 20. Again care is taken so that none of the coating 50 contacts piezoelectric sheet 33 (or piezoelectric device 32, where the latter is preformed before being applied to the substrate). Coating 50 is approximately 0.003 inches thick when applied to the core wire 34 and about 0.001 inches thick when applied to the remaining surfaces around the substrate. The coating 50 is preferably made from a vinyl material, but other conformal materials having suitable insulative properties may also be satisfactorily employed.

An electrically conductive drain wire 52, made for example of gold, is wrapped around coating 50 on core wire 34 and is attached by suitable means to the insulative coating 50 on front surface 22. Drain wire 52 is preferably about 0.0007 inches in diameter, although the size of the wire can vary.

An electrically-conductive coating 54 completely covers insulative coating 50, drain wire 52, as well as the piezoelectric sheet 33 (where the top surface of the sheet is exposed) so as to completely encapsulate the entire assembly with an electrical conductor. Where device 32 is preformed with electrodes prior to mounting the device on the substrate, the upper exposed surface of the device will already be provided with an electrically conductive material so that coating 54 need only extend over the top edges of the front, rear, left and right side surfaces of the transducer so as to electrically contact the edge portions of upper exposed electrode of piezoelectric device 32. Thus, conductive coating 54 covers drain wire 34 and insulative coating 50 on core wire 34 (so as to form the outer conductor of the coaxial line 36). The conductive coating 54 (together with the upper electrode of the device 32) also encases the substrate and piezoelectric sheet 33 so as to form an electric shield as well as a conductor for providing an electrical path between the top side of the sheet 33 of the piezoelectric device 32, and the outer conductor of the coaxial line 36. Conductive coating 54 is preferably made from a silver-filled, RTV paint, and is preferably less than 0.001 inches thick, although other materials and thicknesses may be utilized.

The construction of the transducer is that of an electrical cavity fed by a co-axial conduction line. The combination, when functioning as a transmitter, will contain all electromagnetic fields introduced by way of the co-axial arrangement to the inside of the co-axial line and the electrical cavity. When the combination functions as a receiver, all external electromagnetic fields will be excluded from the inside of both the electrical cavity and the co-axial line, and thus, will exhibit an immunity to incidental fields. When two such transducers are utilized together, one as a transmitter and the other as a receiver, as is contemplated in accordance with at least one aspect of the present invention, the combined effect of driver field retention or trapping and exterior field rejection results in extremely low electrical and magnetic cross talk between transmitter and receiver.

To use the transducer shown in FIG. 1 in the transmit mode of the imaging system described in the Parent Application, an electrical excitation voltage, preferably in the form of a train of pulses, is applied between the electrodes provided in contact with top and bottom surfaces of the piezoelectric sheet 33 (in the embodiment illustrated the top electrode is provided by the conductive coating 54 covering the sheet 33, while the bottom electrode is provided by the coating 30 provided between the top surface 24 of the substrate 20 and the bottom surface of the piezoelectric sheet 33), wherein one electrical path for applying the excitation voltage is formed by the core wire 34 of coaxial line 36, through conductive glue 38 to coating 30 on front surface 22, and in turn to coating 30 on top surface 24 (which directly contacts the lower side of the sheet 33 or directly contacts the lower electrode of the device 32, where the latter is preformed before being mounted to the substrate). The other conductive path for applying the electrical excitation voltage is provided through conductive coating 54 over the outer conductor of the coaxial line 36 and directly to the top surface of the piezoelectric device 32. In accordance with the well known operating characteristics of piezoelectric materials, piezoelectric sheet 33 converts electrical energy from the excitation voltage applied to the sheet to mechanical energy. More specifically, as is also well known, the application of an excitation voltage to piezoelectric material causes the latter to mechanically distort so as to generate an ultrasonic signal in a direction normal to top surface 24.

The drain wire 52 provides a more highly conductive ground path than would be provided by the coating 54 alone. The wire 52 provides longitudinal conductivity while coating 54 provides lateral conductivity.

When the transducer is operated in the receive mode, acoustic pulses which contact piezoelectric device 32 slightly distort the device causing a potential to develop across the top and bottom electrodes (formed in the embodiment shown by coatings 54 and 30, respectively). As is well known, the potential varies with the strength of the acoustic pulse. The potential generated by piezoelectric device 32 is sensed through one conductive path defined by the coating 30 on top surface 24 to side surface 22 and through conductive glue 38 to core wire 34, and through the other conductive path defined by the conductive coating 54. The potential will be proportional to the acoustic pulse sensed. By connecting core wire 34 and the outer coating 54 of the coaxial line 36 to a response circuit (not shown) the sensed voltage can be amplified and processed as described in the Parent Application.

In connection with the following description of the method of making the transducer of the present invention, reference should be made to FIGS. 2-8.

Figure 2:
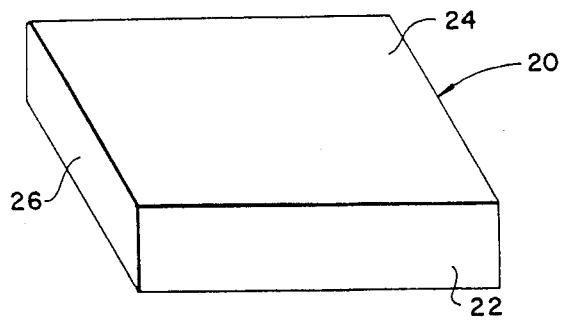
FIGS. 2-8 are schematic, perspective views of successive intermediate products provided in successive steps of the preferred process of fabricating the transducer shown in FIG. 1.

A core or substrate 20 is provided as the starting material as shown in FIG. 2. The substrate is cut or otherwise formed to the required size.

Figure 3:
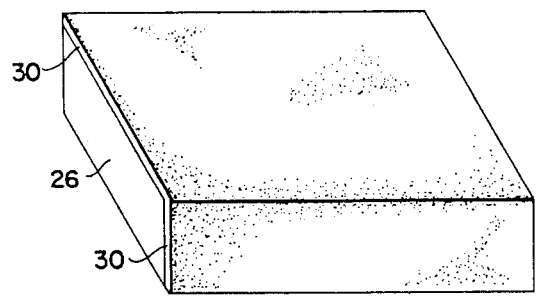

In the second step, as illustrated in FIG. 3, front surface 22 and top surface 24 are provided with a continuous electrically conductive layer 30. As noted above, a metallized cladding may be used to form coating 30. Preferably, the coating is applied to a thickness of about 0.2 mil inches.

Figure 4:
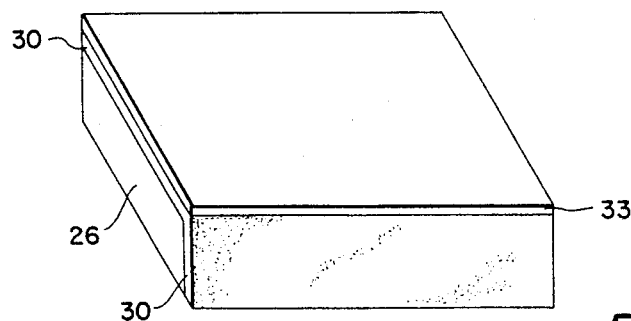

For the third step, as illustrated in FIG. 4, where sheet 33 of piezoelectric material is provided in sheet form, it is applied to the layer 30 provided on top surface 24 using an electrically conductive epoxy to secure the bottom surface of the sheet 33 to the top surface of the layer 30. Alternatively, the material may be applied directly to coating 30 as a coating of piezoelectric material using well known deposition techniques. Where device 32 is preformed with electrodes such as the PVDF foil described above, the bottom electrode is secured to the layer 30 with a suitable electrically conductive material, such as an electrically conductive epoxy. As discussed above, piezoelectric device has an acoustic impedance which is close to that of water and body fluids. Piezoelectric device 32 is preferably sized to cover the entire top surface 24 of the substrate when it is secured to the coating 30 on that surface.

Figure 5:
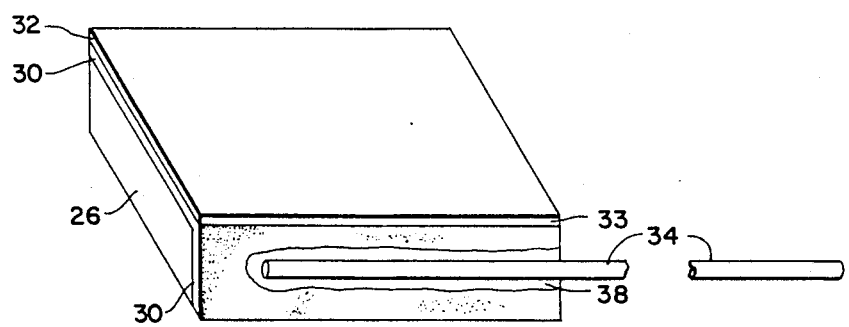

As the fourth step, as illustrated in FIG. 5, one end of core wire 34 is attached to electrically conductive coating 30 on front surface 22 using an electrically conductive glue 38. It is important that glue 38 be applied to front surface 22 so as not to extend into contact with piezoelectric sheet 33, or when device 32 is preformed before being mounted on the substrate, into contact with the upper surface of the piezoelectric device.

Figure 6:
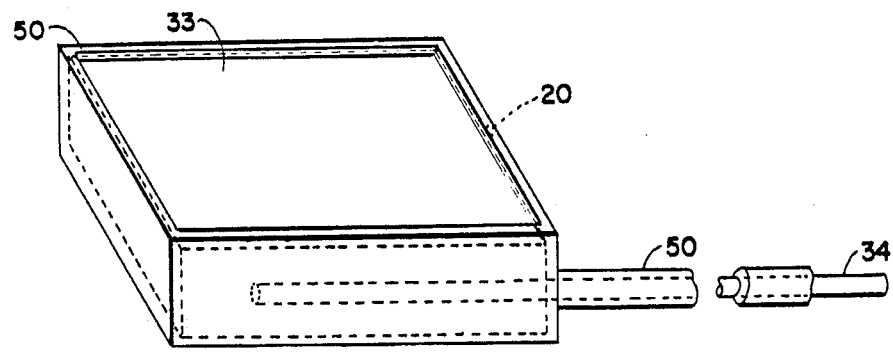

In the fifth step, as illustrated in FIG. 6, core wire 34 and the entire transducer, except for piezoelectric sheet 33 (or device 32), is covered with an electrically insulating conformal coating 50, e.g., a vinyl coating.

Figure 7:
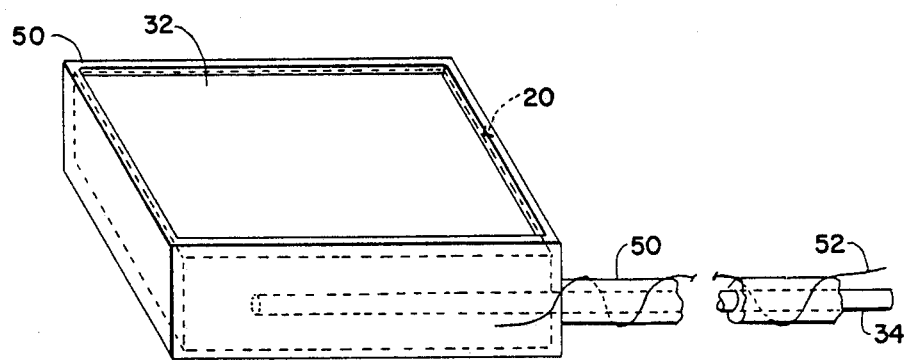

At step six, as illustrated in FIG. 7, gold drain wire 34 is wrapped around the insulative coating 50 on core wire 34 and the end of the wire adjacent the transducer is attached to insulative coating 50 on front surface 22 using an electrically conductive cement.

Figure 8:
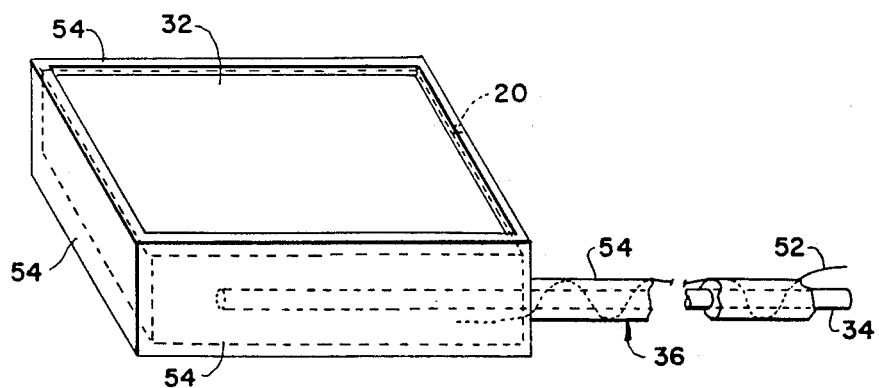

In the final step, as illustrated in FIG. 8, a layer 54 of electrically-conductive paint is applied to all four sides and the bottom of the transducer, to insulative coating 50 on core wire 34, to the drain wire 52 wrapped around the coated core wire, and where sheet 33 is applied without a top electrode, the entire top surface of the sheet 33. Where the piezoelectric device 32 is preformed, layer 54 is applied to all of the surfaces except the upper electrode, but is applied with respect to that electrode so as to extend over the side surfaces of the transducer onto peripheral edge portions of the upper electrode so as to electrically connect the electrically-conductive layer 54 on the sides and bottom of the transducer with piezoelectric device 32 and create the electrical cavity.

Known integrated circuit chip and miniature electronic component fabrication techniques may be satisfactorily employed in the above-described method of manufacturing the transducer of the present invention. For instance, electrically-conductive layers 30 and 54 and insulative layer 50 may be applied using known mask and spray techniques. Piezoelectric sheet 33 may be applied using known vacuum workpiece positioning systems.

Figure 9:
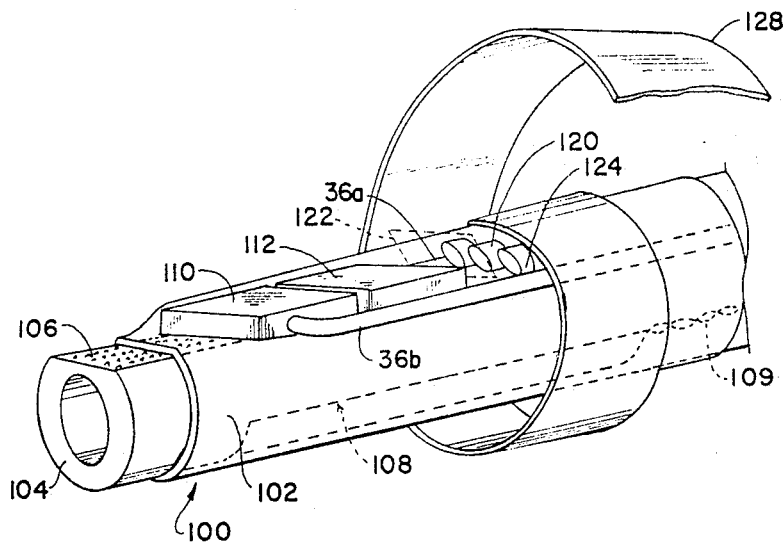
FIG. 9 is a perspective view of the tip portion of the distal end of the catheter of the type used in the imaging system described in the Parent Application, and incorporating the present invention.
Figure 10:
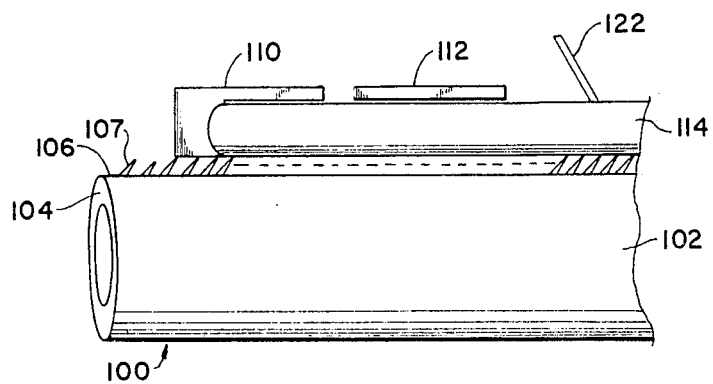
FIG. 10 is a side elevation view of the tip portion of the catheter shown in FIG. 9.

Referring next to FIGS. 9 and 10, in accordance with another aspect of the present invention, a catheter probe 100 includes a pair of the transducers of the present invention and is designed for use in a system for imaging internal features of a body part, such as the system described in the Parent Application.

The catheter probe 100 of the present invention comprises an flexible tubular body having a distal end 104 and a flat surface 106 for supporting each transducer 110 and 112. The flat surface extends along a portion of the length of body and is formed adjacent distal end 104. As best seen in FIG. 10, flat surface 106 is treated, preferably when initially formed, to provide a roughened surface so as to create dead air spaces between the catheter and each transducer 110 and 112.

As described in the Parent Application, a loop of wire 108 is attached to the body at the distal end 104. Loop 108 is provided as an antenna for detecting magnetic reference signals used in establishing the position of the distal end of the catheter probe 100 inside the body part being imaged.

Catheter probe 100 further comprises transmit transducer 110 and receive transducer 112, each constructed as described with respect to FIGS. 1-8. The two transducers are positioned on probe 100 so the bottom surfaces of the transducers rest on the roughened surface formed on flat surface 106. Where the catheter body is formed of a high modulus nylon, such as the nylon material sold under the trademark Zitel 42, the roughened surface 106 can be mechanically formed, for example, by using a fine grain sand paper to rub the flat surface so as to create randomly dispersed burrs or irregular cuts on the surface with hanging fragments at least in the area which will support the transducers 110 and 112. Because of the close range of the target, the transducers 110 and 112 are positioned adjacent to, but spaced apart slightly, e.g., about 0.006 inches, from one another. The coaxial line 36a provides the excitation voltage to the transmit transducer 110, while coaxial line 36b provides signals representative of the acoustic energy 20 sensed by receive transducer 112. Coaxial wires 36a and 36b are positioned to extend along the surface of the body, away from distal end 104.

Probe 100 also comprises one or more optical waveguides 120 for transmitting laser energy toward distal end 104 to a position adjacent receive transducer 112. A mirror 122 is positioned between transducer 112 and the output ends 124 of waveguides 120 for directing the laser energy transmitted by waveguides 120 so as to travel in a direction substantially parallel to the direction of an axis normal to the upper surface of the transducer 112 and transverse to the axis of the catheter.

In order to secure the two transducers in place on the catheter probe, the entire end portion of catheter probe 100 including the two transducers, is wrapped in a thin film 102. The selection of material for the film 102 should have an acoustic impedance which closely approximates the geometric mean of the acoustic impedances of the transducer piezoelectric device 32 and the bodily fluids in contact with the film in order to improve the acoustic coupling between the device 32 and the fluids. The foregoing is easily accomplished with any one of several plastic films, with polyethylene being preferred. The plastic film functions as a one-quarter wave anti-reflective intervening layer of plastic material between each transducer and the body tissues disposed over the transducer at the particular location of the device. The preferred polyethylene film can be provided with a coating of suitable gummed adhesive on its inner surface so as to ensure the film remains in a wrapped condition.

A wrap 128 covers the remaining portions of the catheter end not covered by the film 102 and therefore does not cover the transducers.

Coaxial lines 36a and 36b, antenna loop 108, and optical waveguides 120 are encased in film 128 and extend away from distal end 104 of probe 100 extending along the body 102 of the catheter. These wires and optical fibers are enclosed as a bundle in a suitable casing. This encased bundle is connected to a control device (not shown) for generating the excitation voltage supplied over coaxial wire 36a to transmit transducer 110, for receiving the response signal from receive transducer 112 carried over coaxial line 36b, for generating the laser energy transmitted over optical waveguides 120, and for receiving signals over wire ends 109 from wire loop 108.

It is important that transducers 110 and 112 be positioned as close to one another as possible so that the receive transducer 112 is positioned to receive echo pulses from relatively close targets in response to acoustic pulses generated by the transmit transducer 110. The electrical cavity construction of the transducer of the present invention permits transducers 110 and 112 to be mounted in side-by-side configuration, as the electrical cavity casing around the transducers substantially prevents electromagnetic fields from leaking out or entering the transducers. As such, the transducers are electromagnetically isolated from one another, with the result that there is little or no electromagnetic interference between transducers 110 and 112.

It is equally important that transducers 110 and 112 be acoustically isolated from one another. Because acoustic cross talk arrives later in time than electrical cross talk it can arrive at the receiving transducer at the same time as the echo data signals and therefore make it even more difficult to process the latter signals. By roughening the flat surface 106, the transmit and receive transducer 110 and 112 are mounted so as to be substantially acoustically isolated from one another because the roughened surface provides sufficient dead air space between the bottom surface of each transducer and the surface 106 so as to substantially acoustically dampen any acoustic signals which might be transmitted between the two transducers through the body 102. The acoustic dampening virtually eliminates any detrimental acoustic cross talk between the transducers.

Catheter probe 100 is used in substantially the same manner as the catheter probe of the imaging system disclosed in the Parent Application. Thus, attention is directed to the Parent Application for a complete description of the manner in which probe 100 is used. Briefly, however, the distal end of the catheter probe 100 is inserted in a selected body part, e.g., a coronary artery, until the probe is positioned at an area of interest. The signals received on wire loop 108 are used in determining the radial position of probe 100. The receive transducer senses the axial position of the probe. Acoustic pulses are transmitted from transmit transducer 110 and the associated echo pulses are sensed by receive transducer 112. Pursuant to the information received from receive transducer 112 and wire loop 108, an image of the internal features of the body part can be generated. Using this image, laser energy can transmitted along optical waveguide 120, and folded at mirror 122 so as to selectively radiate preselected portions of the portion of the body under investigation. This laser energy can be used, for instance, to burn away plaque deposits inside a coronary artery.

A significant advantage of the transducer of the present invention is that two of the transducers can be positioned adjacent one another without substantially electromagnetically interfering with one another. The electrical isolation provided by the electrical cavity and coaxial construction of the transducers greatly reduces or eliminates electrical cross talk between the transducers. As such, the transducer of the present invention is highly suited for use, in side-by-side configuration, particularly for close range ranging systems such as the system disclosed in the Parent Application. Further, by mounting the transducers on a roughened surface of the catheter, the two transducers can be substantially acoustically isolated from one another so as to substantially reduce the effects of acoustical cross-talk between the two transducers so that the two transducers 110 and 112 can be mounted very close to one another without interfering with one another.

Because the piezoelectric material used for piezoelectric sheet 33 is substantially acoustically matched to the body fluids, the transducers can be made miniature in size so as to fit on the distal end of the catheter probe. Consequently, the use of miniature transducers makes the use of the probe as part of the imaging system described in the Parent Application practical. The method of manufacturing the transducer of the present invention is designed to permit rapid and efficient fabrication of the miniature transducer, transducer for example, having miniature external dimensions in the range of 0.012" (thickness) ×0.028" (width) ×0.038" (length-along the length of the catheter). It is believed that the transducer can be made even smaller than these dimensions with, for example, improved copolymer materials for sheet 33 providing an even closer match in acoustic impedance (so as to allow a decrease in the thickness dimension) and increased signal strength per unit area (so as to allow a decrease in the thickness dimension).

An important advantage of the catheter probe of the present invention, as compared to known ultrasonic probes having a single transducer for transmitting and receiving acoustic pulses, is that the present catheter probe will provide accurate imaging data of internal body features at extremely close range, where in some cases the outer surface of the film 128 above the upper surface of the piezoelectric device 32, directly contacts a surface of interest. With single ultrasonic transducer probes, the minimum range of the devices is typically between about a few millimeters to 10 centimeters or so.

Since certain changes may be made in the above product, method and apparatus without departing from the scope of the invention herein involved, it is intended that all matter contained in the above description or shown in the accompanying drawings shall be interpreted in an illustrative and not in a limiting sense.

What is claimed is:

1. A method of making a transducer of the type including (a) a substrate having a first surface for supporting a piezoelectric device including a sheet of piezoelectric material, and (b) a coaxial line having an inner and outer conductor for providing a potential to opposite sides of said sheet of piezoelectric material, said method comprising the steps of:

mounting said sheet of piezoelectric material on said first surface of said substrate so that one side of said sheet and said first surface mutually confront one another;

electrically coupling the center conductor of said coaxial line to said one side of said sheet;

encasing the entire substrate, except for said first surface, with a first layer of an electrically insulative material so that said first layer is attached to said substrate; and applying a second layer of electrically conductive material so as to (1) attach said second layer to said first layer of electrically insulative material so as to cover said first layer, (2) form an electrical path between the outer conductor of said coaxial line and the other side of said sheet of piezoelectric material and (3) completely encase said substrate and said sheet of piezoelectric material in an electrically conductive material so that said substrate and sheet are electrically shielded.

2. The method according to claim 1, wherein said step of mounting said sheet includes the step of applying an electrically conductive material to at least a portion of said first surface of said substrate and securing said sheet so that said one side of said sheet is in electrical contact with said electrically conductive material.

3. The method according to claim 2, wherein said substrate includes a second surface, and said step of applying said electrically conductive material includes the step of applying said electrically conductive material to said second surface of said substrate so as to be in electrical contact with the electrically conductive material on said first surface, and said step of electrically coupling said center conductor includes the step of connecting said center conductor to the electrically conductive material on said second surface.

4. The method according to claim 3, wherein said step of applying said electrically conductive material to said first and second surfaces includes the step of completely covering said first and second surfaces with a layer of said electrically conductive material.

5. The method according to claim 4, wherein said step of mounting said sheet includes the step of securing said one side of said sheet directly to said layer of electrically conductive material on said first surface so that said layer functions as an electrode for said piezoelectric device.

6. The method according to claim 4, wherein said step of electrically connecting said center conductor to the electrically conductive material on said second surface includes the step of gluing said conductor to said electrically conductive material.

7. The method according to claim 6, wherein said step of gluing said conductor to said electrically conductive material includes securing said conductor to said electrically conductive material with an electrically conductive glue.

8. The method according to claim 3, wherein said electrically conductive material is metal cladding, and said step of mounting said sheet of piezoelectric material on said first surface includes the step of securing said one side of said sheet to said metal cladding on said first surface.

9. The method according to claim 3, wherein said step of applying said electrically conductive material to said first surface includes the step of completely covering said first surface with a layer of said electrically conductive material.

10. The method according to claim 3, wherein said step of coating also includes the step of coating the center conductor of said coaxial line with said first layer of electrically insulative material.

11. The method according to claim 10, wherein said step of applying said second layer of electrically conductive material also includes the step of applying said second layer to the first layer of electrically insulative material coated on said center conductor so as to form said outer conductor of said coaxial line integrally with said second layer of electrically conductive material applied on said first layer of electrically conductive material coated on said substrate.

12. The method according to claim 11, wherein said second layer of electrically conductive material also includes the step of covering the other side of said sheet of piezoelectric material with said second layer so as to form an electrode of said piezoelectric device.

13. The method according to claim 12, wherein said sheet of piezoelectric material is provided with a pair of electrodes respectively disposed on opposite sides of said sheet so as to form said piezoelectric device prior to mounting said sheet on said first surface of said substrate, and said step of applying said second layer of electrically conductive material includes the step of applying said second layer of electrically conductive material in electrical contact with peripheral portions of the electrode formed on the other side of said sheet of piezoelectric material.

14. The method according to claim 13, wherein said step of applying said second layer includes the step of painting said second layer on said first layer of electrically conductive material and said peripheral portions of the other side of said sheet with an electrically conductive paint.

15. The method according to claim 11, further including the step of winding a drain wire around said first layer of electrically insulative material coated on said center conductor prior to said step of applying said second layer of electrically conductive material so that said drain wire is electrically coupled to said second layer of electrically conductive material coated over said first layer of electrically insulative material coated on said substrate.

16. A method of making a transducer of the type including a substrate having top, bottom, and side surfaces, the method comprising the steps of:

applying a first layer of electrically conductive material to said top surface and at least a portion of one of said side surfaces such that an electrical path is provided through said first layer between said top and said one side surface;

attaching a sheet of piezoelectric material to said top surface such that said first layer is in electrical contact with one side of said sheet;

electrically connecting a first electrically conductive wire to said first layer applied to said one side surface;

applying a layer of electrically insulative material over said first wire and said side and bottom surfaces;

wrapping a second electrically conductive wire around said layer of electrically insulative material on said first wire;

coating at least said
  (a) second wire, and
  (b) said layer of insulative material on said first wire, and said bottom and side surfaces,
with a second layer of electrically-conductive material so that said second layer is electrically connected to the other side of said sheet of piezoelectric material as to totally encase said substrate, said sheet of piezoelectric material and said core wire in electrically conductive material.

17. The method according to claim 16, wherein said step of wrapping said second electrically conductive wire further includes the step of securing the end of said second wire to said layer of electrically insulative material on said substrate.

18. The method according to claim 16, wherein said step of applying said first layer to said top and one side surface includes the step of applying an electrically conductive material as a substantially uniform layer on said top and one side surface.

19. The method according to claim 18, wherein said step of applying said material as a substantially uniform layer includes the step applying a layer of metal cladding about 0.2 mil inches thick.

20. The method according to claim 16, wherein said step of electrically connecting said first wire to said first layer includes the step of gluing said first wire to said first layer.

21. The method according to claim 20, wherein the step of gluing includes the step of securing said first wire to said first layer using a silver-filled room temperature vulcanizing glue.

22. The method according to claim 16, wherein said step of coating said second layer of electrically conductive material includes the step of painting an electrically-conductive paint on said second wire, said layer of insulative material on said first wire and said bottom, and side surfaces, and said other side of said sheet of piezoelectric material.

* * * * *